(12) United States Patent
Tsukada et al.

(10) Patent No.: US 12,364,858 B2
(45) Date of Patent: Jul. 22, 2025

(54) BIOLOGICAL ELECTRODE AND CARDIAC PACEMAKER

(71) Applicant: NIPPON TELEGRAPH AND TELEPHONE CORPORATION, Tokyo (JP)

(72) Inventors: Shingo Tsukada, Musashino (JP); Tetsuhiko Teshima, Musashino (JP); Hiroshi Nakashima, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 275 days.

(21) Appl. No.: 17/769,965

(22) PCT Filed: Oct. 29, 2019

(86) PCT No.: PCT/JP2019/042392
§ 371 (c)(1),
(2) Date: Apr. 18, 2022

(87) PCT Pub. No.: WO2021/084622
PCT Pub. Date: May 6, 2021

(65) Prior Publication Data
US 2022/0355103 A1 Nov. 10, 2022

(51) Int. Cl.
*A61N 1/00* (2006.01)
*A61N 1/05* (2006.01)
*A61N 1/362* (2006.01)

(52) U.S. Cl.
CPC ........... *A61N 1/0597* (2013.01); *A61N 1/362* (2013.01)

(58) Field of Classification Search
None
See application file for complete search history.

(56) References Cited

U.S. PATENT DOCUMENTS

| | | | |
|---|---|---|---|
| 2006/0183989 A1* | 8/2006 | Healy | A61B 5/24 607/152 |
| 2008/0097280 A1* | 4/2008 | Martin | A61K 9/0009 604/21 |
| 2008/0161893 A1* | 7/2008 | Paul | A61B 18/14 607/116 |
| 2014/0343392 A1* | 11/2014 | Yang | A61B 5/7221 600/393 |
| 2018/0008817 A1* | 1/2018 | Ejiri | A61N 1/0484 |
| 2019/0088382 A1* | 3/2019 | Allen | B82Y 40/00 |

OTHER PUBLICATIONS

Y.B. Benovitski et al., "Ring and Peg Electrodes for Minimally-Invasive and Long-Term Sub-scalp EEG Recordings", Epilepsy research, Jun. 2017, 135: 29-37.

* cited by examiner

*Primary Examiner* — John R Downey
*Assistant Examiner* — Anant A Gupta
(74) *Attorney, Agent, or Firm* — Harness, Dickey & Pierce, P.L.C.

(57) ABSTRACT

The present biological electrode includes a conductive fabric (2) formed of base fibers which are filled with a conductor and/or to which the conductor is adhered, a thin metallic wire (3) formed into a spiral shape and covered with the conductive fabric (2) from a side of a distal end in an axis direction, and a filling material (5) with which a gap between the conductive fabric (2) and the thin metallic wire (3) is filled and which supports the conductive fabric (2) and the thin metallic wire (3), and the conductor is electrically connected with the thin metallic wire (3).

13 Claims, 4 Drawing Sheets

BIOLOGICAL ELECTRODE AND CARDIAC PACEMAKER

CROSS-REFERENCE TO RELATED APPLICATIONS

This application is a 371 U.S. National Phase of International Application No. PCT/JP2019/042392 filed on Oct. 29, 2019. The entire disclosure of the above application is incorporated herein by reference.

TECHNICAL FIELD

The present invention relates to a biological electrode and a cardiac pacemaker.

BACKGROUND ART

In related art, in order to receive an electric signal accurately and efficiently in a living body at an external device and conversely to transmit an electric signal from an external device into a living body, a biologically implanted biological electrode has been used.

A biologically implanted biological electrode has widely been used for a cardiac pacemaker, a cochlear implant, and so forth. Further, as a future human interface, development of a brain-machine interface and so forth using an implanted biological electrode has been progressing.

As an example of a biologically implanted biological electrode, Non-Patent Literature 1 discloses a biological electrode in which an electrode portion is in a peg or ring shape.

CITATION LIST

Non-Patent Literature

Non-Patent Literature 1: Benovitsk et al., "Ring and peg electrodes for minimally-Invasive and long-term sub-scalp EEG recordings", Epilepsy Res. 2017 135: 29-37.

SUMMARY OF THE INVENTION

Technical Problem

However, a problem is that in a case where an electrode portion is made of hard metal such as stainless steel, a pressure is applied to a biological tissue due to contact with the electrode portion, and a wearer of the electrode is thereby caused to experience discomfort.

In consideration of the above situation, an object of the present invention is to provide a biological electrode that can reduce a pressure applied to a biological tissue and can maintain a function of an electrode even when being worn.

Means for Solving the Problem

One aspect of the present invention provides a biological electrode including: a conductive fabric formed of base fibers which are filled with a conductor and/or to which the conductor is adhered; a thin metallic wire formed into a spiral shape and covered with the conductive fabric from a side of a distal end in an axis direction; and a filling material with which a gap between the conductive fabric and the thin metallic wire is filled and configured to support the conductive fabric and the thin metallic wire, in which the conductor is electrically connected with the thin metallic wire.

Effects of the Invention

The above biological electrode can provide a biological electrode that can reduce a pressure applied to a biological tissue and can maintain a function of an electrode even when being worn.

DESCRIPTION OF EMBODIMENTS

An embodiment of the present invention will be described with reference to FIG. 1 to FIG. 4.

A biological, electrode 1 according to the present embodiment is an electrode used for sensing and so forth (including sensing, pacing, and transmission and reception of an electric signal) in a cardiac pacemaker, a cochlear implant, a brain-machine interface, or the like, for example. That is, the biological electrode 1 according to the present embodiment may be used for a cardiac pacemaker, a cochlear implant, a brain-machine interface, or the like. The biological electrode 1 according to the present, embodiment may be used for a device performing sensing and so forth of a biological organ which expands and contracts such as a heart or a skeletal muscle.

Figure 1:
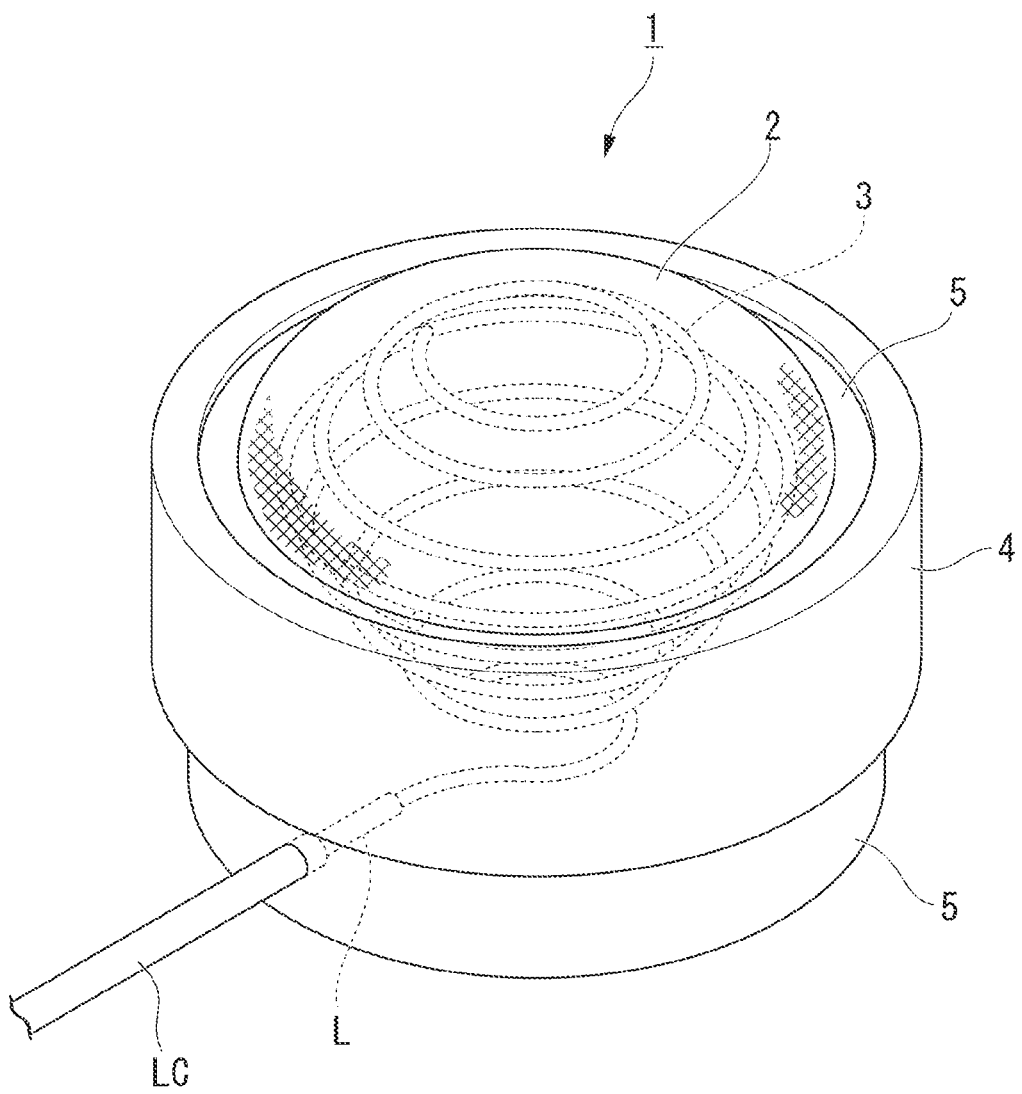
FIG. 1 is a perspective view of a biological, electrode according to an embodiment, of the present invention.
Figure 2:
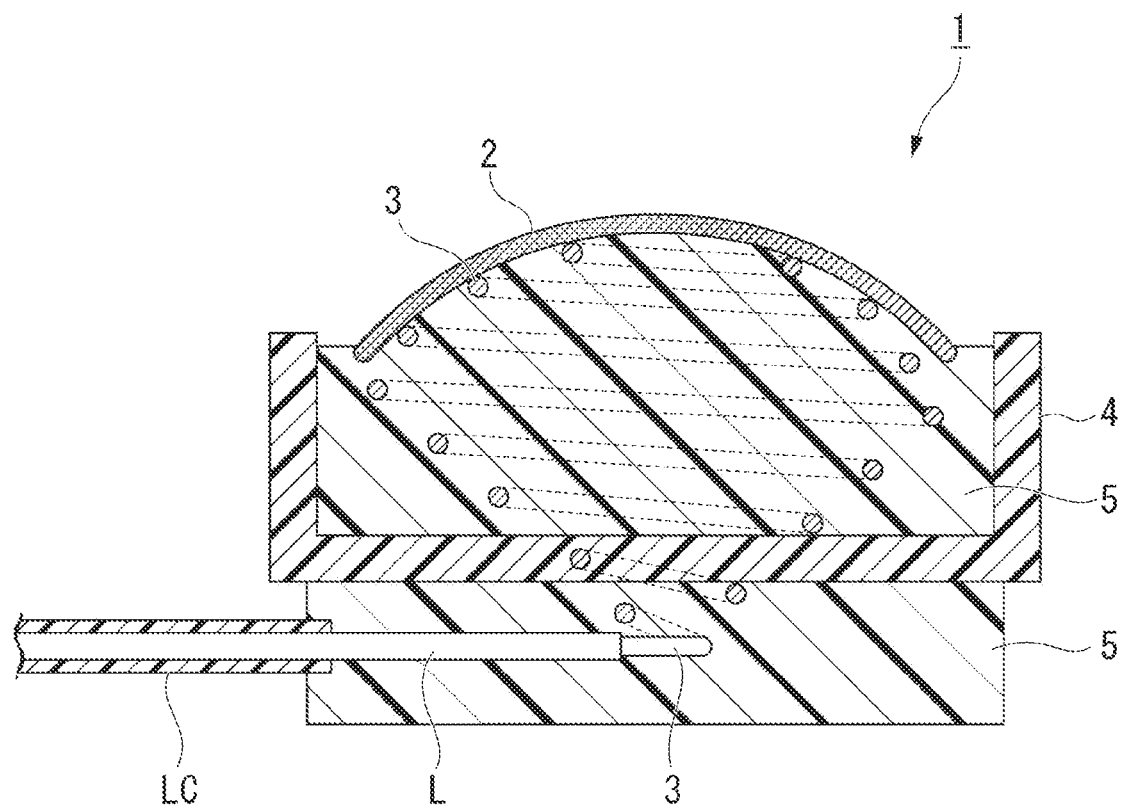
FIG. 2 is a cross-sectional view of the biological electrode according to an embodiment of the present invent ion.

As illustrated in FIG. 1 and FIG. 2, the biological electrode 1 includes a conductive fabric 2, a thin metallic wire 3, a pedestal 4, and a filling material 5.

The conductive fabric 2 is formed of base fibers which are filled with a conductor containing conductive polymers and/or to which the conductor is adhered. Conductive polymers are used as the conductor, and the rigidity of the conductive fabric 2 can be made lower than a case where a metal material is used as the conductor. In the present embodiment, the conductive fabric 2 has a generally circular shape but may have an elliptical shape, a quadrangular shape, another polygonal shape, or the like as long as the shape has a certain surface area.

A formation method of the conductive fabric 2 may be formation by knitting, formation by weaving, formation as a non-woven fabric, using one kind of these, or using a combination of two or more kinds of those.

As the conductive polymers used for the conductive fabric 2, a polythiophene-based conductive polymer such as PEDOT-PSS {poly(3,4-ethylenedioxythiophene)-poly(styrene sulfonate)}, polyacetylene based, polyaniline based, and polypyrrole-based conductive polymers, and so forth are used.

The conductor used for the conductive fabric 2 may contain an additive other than the conductive polymers. As additives, for example, glycerol, sorbitol, polyethylene glycol-polypropylene glycol copolymer, ethylene glycol, sphingosine, phosphatidylcholine, and so forth are raised. The additive contained in the conductor may be one kind, or two or more kinds may be used in combination.

The additives of the above examples can be used for the purpose of adjusting wetting characteristics of the conductive fabric 2 or can be used, by giving flexibility, for the purpose of improving affinity for a biological tissue (skin or tissue) in use as the biological electrode.

Note that as specific examples of adjustment of the wetting characteristics, for example, adjustment of water absorbency, prevention of excessive swelling or shrinkage in moistening or drying, and so forth are raised.

As the base fibers used for the conductive fabric 2, animal fibers such as silk and animal hairs, vegetable fibers such as cotton and hemp, synthetic fibers formed of nylon, polyester, acrylic resin, polyvinyl, chloride, polyurethane, and so forth, mixed spun fibers and regenerated fibers of those, and so forth are used.

As a method for filling the base fibers with the conductor or adhering conductor to the base fibers, a method of filling gaps of the base fibers with the conductor, a method of covering the base fibers by the conductor, a method of intertwining the base fibers with the conductor formed into a fiber-like state, or a method of combining chose together can be applied.

Polythiophene-based, polyacetylene-based, polyaniline-based, and polypyrrole-based conductive polymers have excellent conductivity and hydrophilicity. PEDOT-PSS as one kind of polythiophene-based conductive polymer particularly has excellent conductivity, hydrophilicity, and biocompatibility and have excellent adhesiveness to synthetic fibers of silk, polyester, and so forth. Consequently, the conductive fabric 2 using PEDOT-PSS as the conductive polymers and using synthetic fibers of silk, polyester, and so forth as the base fibers have excellent biocompatibility, conductivity, flexibility, and strength together.

The thin metallic wire 3 is formed into a spiral shape and has a spring-shaped structure. The thin metallic wire 3 is covered with the conductive fabric 2 from a distal end side in an axis direction. Note that in the present embodiment, the thin metallic wire 3 is covered with the base fibers, and the base fibers are thereafter filled with the conductor. Thus, the conductor is fused with the thin metallic wire 3 at the same time as formation of the conductive fabric 2. The thin metallic wire 3 is fused with the conductor, and the conductivity of the biological electrode 1 is thereby improved.

As the thin metallic wire 3, a material having high biocompatibility is used, and for example, a platinum-iridium alloy, platinum, gold, titanium, silver, a cobalt alloy, a nickel alloy, carbon fiber, stainless steel, or the like is used.

A base end of the thin metallic wire 3 is connected with a lead wire L of a cardiac pacemaker or the like, for example. The thin metallic wire 3 and the lead wire L are connected together by using a crimping sleeve or the like, for example.

In order to secure durability, reliability, and safety, a similar material to the thin metallic wire 3 is preferably used for the lead wire L, and the lead wire L is preferably formed into a coil shape or a twisted wire shape.

The pedestal 4 has a general saucer shape having a recess on the conductive fabric 2 side. As a material of the pedestal 4, a silicone material such as PDMS (polydimethylsiloxane) is used.

The pedestal 4 is formed to have a thickness of approximately 1 mm. The recess of the pedestal 4 is formed to have a diameter of approximately 4 mm and a depth of approximately 2 mm. Further, the conductive fabric 2 covering the thin metallic wire 3 is arranged to be exposed from the recess of the pedestal 4, and the pedestal 4 is formed such that the height, of the conductive fabric 2 exposed from the recess of the pedestal 4 falls in a range of approximately 0.5 mm to 2 mm.

The pedestal 4 is provided between the distal end and the base end of the thin metallic wire 3, and the thin metallic wire 3 passes through the pedestal 4.

Gaps among the conductive fabric 2, the thin metallic wire 3, the pedestal 4, and the lead wire L are filled with the filling material 5, and the filling material 5 supports the conductive fabric 2, the thin metallic wire 3, the pedestal 4, and the lead wire L. As the filling material 5, a silicone material such as PDMS is used.

Figure 3:
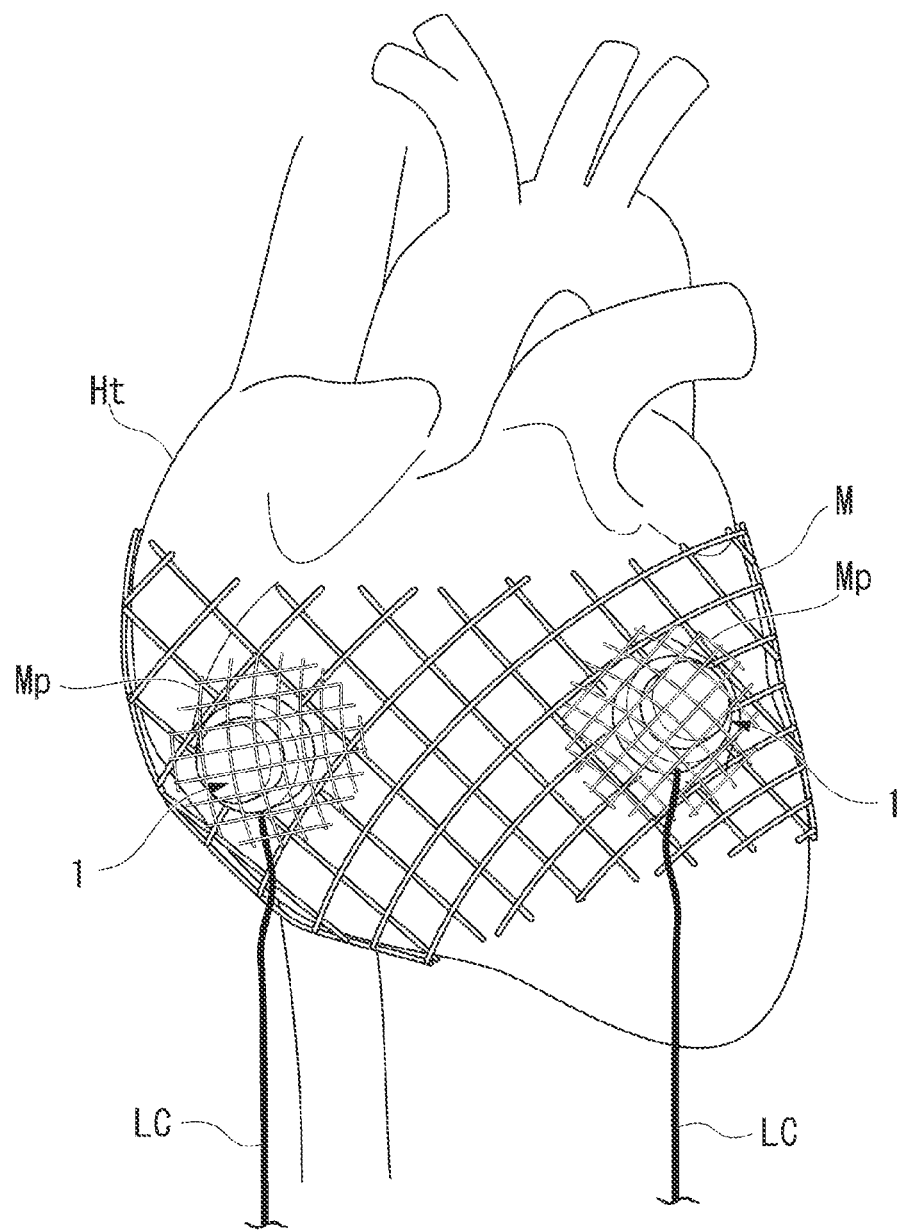
FIG. 3 is a diagram illustrating a case where the biological electrode according to an embodiment of the present invention is installed as a cardiac pacemaker.

Next, an action of the biological electrode 1 will be described. As illustrated in FIG. 3, the biological electrode 1 is inserted in a pocket Mp formed in a mesh M mounted on an installation target part of the biological electrode 1 and thereby installed, for example. As a material of the mesh M, polyester, silk, or the like is used. The biological electrode 1 used as an anode and the biological electrode 1 used as a cathode are installed.

Figure 4:
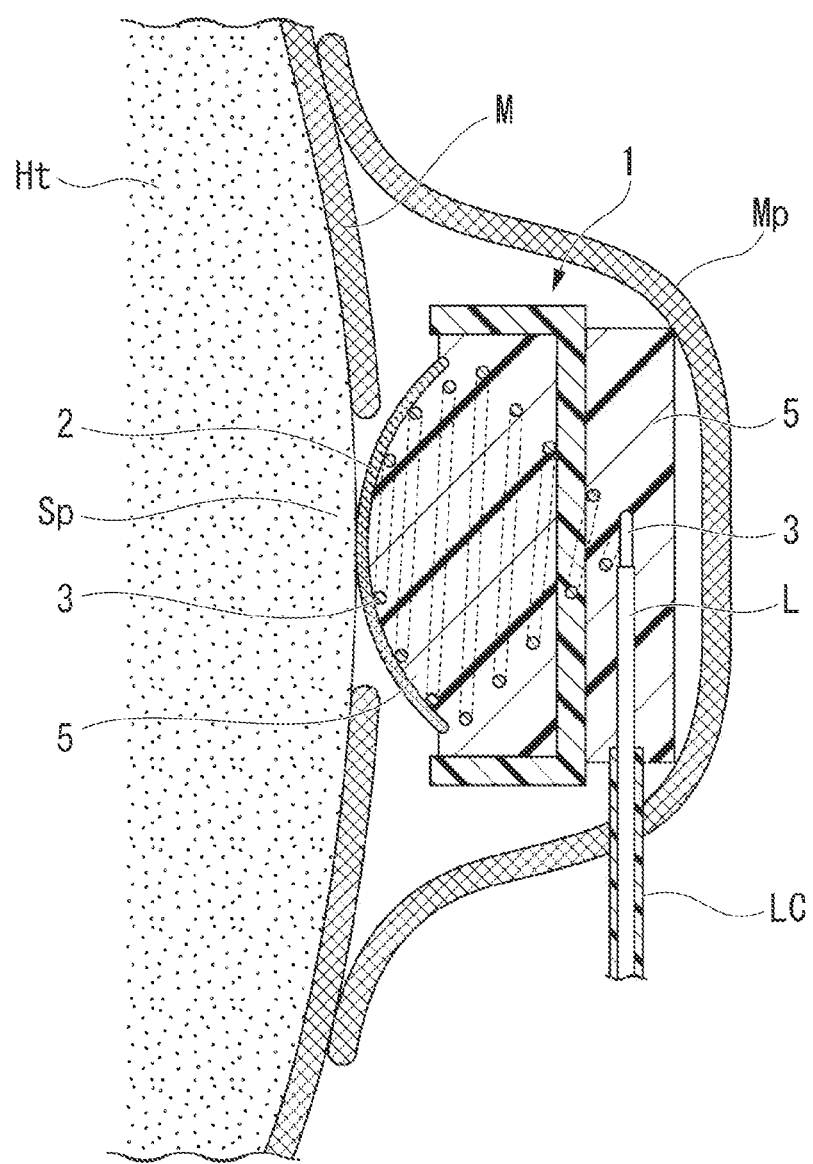
FIG. 4 is a cross-sectional view of the biological electrode according to an embodiment, of the present invention which is installed.

As illustrated in FIG. 4, the biological electrode 1 is installed such that the conductive fabric 2 contacts with a sensing-and-so-forth target part Sp.

The biological electrode 1 is installed such that an axis direction of the thin metallic wire 3 generally agrees with an expansion-contraction direction of transformation of the sensing-and-so-forth target part Sp by a pulse.

The biological electrode 1 is installed in such a manner, and the sensing-and-so-forth target part Sp is electrically connected with the conductive fabric 2, the thin metallic wire 3, and the lead wire L which have conductivity.

The biological electrode 1 contacts with the sensing-and-so-forth target part Sp via the conductive fabric 2 which has flexibility by using fibers as a base material. The thin metallic wire 3 formed, into a spiral shape and having a spring-shaped structure is arranged between the sensing-and-so-forth target part Sp and the lead wire L and buffers pressures received from the lead wire L due to pulsation of the sensing-and-so-forth target part Sp.

The biological electrode 1 having the above configuration is installed such that the conductive fabric 2 having flexibility and conductivity contacts with the sensing-and-so-forth target part Sp. Further, in the biological electrode 1, the conductive fabric 2 portion is connected with the lead wire L via the thin metallic wire 3 formed into the spiral shape and having the spring-shaped, structure. Thus, the biological electrode 1 contacts with the sensing and so forth target part Sp while having proper buffering characteristics against transformation of the sensing-and-so-forth target part. Sp which accompanies a pulse and can reduce a pressure exerted on a biological tissue.

In the biological electrode 1, the base fibers of the conductive fabric 2 to contact with the sensing-and-so-forth target part Sp are filled with the conductor, and/or the conductor is adhered to the base fibers, the conductor distributed to the whole conductive fabric 2, and the biological electrode 1 can thus maintain a function of an electrode even when being worn. Because the thin metallic wire 3 of the biological electrode 1 has the spring-shaped structure which is generally coaxial with the direction of transformation of the sensing-and-so-forth target part Sp which accompanies a pulse, a stress produced by a pulse is net concentrated into a specific portion but is dispersed, and fracture and wire breakage are less likely to occur.

Further, the biological electrode 1 is integrally formed by filling the gaps among the conductive fabric 2, the thin metallic wire 3, and the lead wire L with the filling material 5 using a silicone material. Thus, the biological electrode 1 has flexibility and can endure a mechanical stress in installation. In addition, the conductive fabric 2 of the biological electrode 1 draws the filling material 5 by capillary action in filling with the filling material 5. A space between the conductive fabric 2 and the thin metallic wire 3 is filled up with the filling material 5 drawn toward the conductive fabric 2, and insulation between the conductive fabric 2 and the thin metallic wire 3 is thereby enhanced. The insulation between the conductive fabric 2 and the thin metallic wire 3 is enhanced, a spreading amount of a current flowing through the conductive fabric 2 into body fluids is thereby regulated, and loss of current is reduced.

In the foregoing, an embodiment of the present invention has beer described with reference to the drawings. However, specific configurations are not limited to those embodiments, and the present invention includes design changes and so forth made without departing from the scope of the gist of the present invention. Further, it is possible to make configurations by appropriately combining configuration elements which are described in the above-described embodiments and modification examples described in the following.

For example, the thin metallic were 3 of the biological electrode 1 may not only be covered with the conductive fabric 2 but also be sewn into the conductive fabric 2. The thin metallic wire 3 is sewn into the conductive fabric 2, and conductivity is thereby improved.

The conductive fabric 2 is formed by filling the base fibers with the conductor or adhering the conductor to the base fibers, the thin metallic wire 3 is thereafter covered with the conductive fabric 2, the conductor is fused with the thin metallic wire 3, and the biological electrode 1 may thereby be formed.

The thin metallic wire 3 of the biological electrode 1 may be formed into a protruding mesh shape with respect to the conductive fabric 2 and be covered with the conductive fabric 2.

The biological electrode 1 may include a conductor in a protruding plate shape with respect to the conductive fabric 2 instead of the thin metallic wire 3, and the conductor in the protruding plate shape may be covered with the conductive fabric 2.

In the biological electrode 1, instead of the thin metallic wire 3, a conductor formed into a string shape may be used.

In the biological electrode 1, the thin metallic wire 3 may be exposed from the filling material 5. In such a case, a portion or the thin metallic wire 3 is covered, the portion being exposed from the filling material 5.

As long as a shape can be retained only by the filling material 5, the biological electrode 1 may not have to include the pedestal 4.

In the biological electrode 1, the conductive polymers may not have to be contained in the conductor.

In the biological electrode 1, the conductor may not have to be fused with the thin metallic wire 3 as long as the conductor and the thin metallic wire 3 are electrically connected together.

REFERENCE SIGNS LIST 1 biological electrode
2 conductive fabric
3 thin metallic wire
A pedestal
5 filling material
HL heart
L lead
LC cover
M mesh
Mp pocket
Sp sensing-and-so-forth target part

The invention claimed is:

1. A biological electrode comprising:
a conductive fabric formed of base fibers which are filled with a conductor or to which the conductor is adhered;
a thin metallic wire formed into a spiral shape and covered with the conductive fabric from a side of a distal end in an axis direction; and
a filling material with which a gap between the conductive fabric and the thin metallic wire is filled and configured to support the conductive fabric and the thin metallic wire, wherein the thin metallic wire has a spiral spring-shaped structure along the axis, and the conductor is electrically connected with the thin metallic wire;
wherein the distal end of the thin metallic wire forms a convex shape protruding outwardly in the axis direction and the conductive fabric covering the distal end of the thin metallic wire mimics the convex shape protruding outwardly in the axis direction.

2. The biological electrode according to claim 1, wherein the conductor contains conductive polymers.

3. The biological electrode according to claim 2, wherein the conductive polymers contain any of polythiophene-based, polyacetylene-based, polyaniline-based, or polypyrrole-based conductive polymers.

4. The biological electrode according to claim 1, further comprising a pedestal that is formed between the distal end and a base end of the thin metallic wire and supports the conductive fabric and the thin metallic wire.

5. A cardiac pacemaker comprising the biological electrode according to claim 1.

6. The biological electrode according to claim 2, further comprising a pedestal that is formed between the distal end and a base end of the thin metallic wire and supports the conductive fabric and the thin metallic wire.

7. The biological electrode according to claim 3, further comprising a pedestal that is formed between the distal end and a base end of the thin metallic wire and supports the conductive fabric and the thin metallic wire.

8. The cardiac pacemaker according to claim 5, wherein the conductor of the biological electrode contains conductive polymers.

9. The cardiac pacemaker according to claim 5, wherein the conductive polymers of the biological electrode contain any of polythiophene-based, polyacetylene-based, polyaniline-based, or polypyrrole-based conductive polymers.

10. The cardiac pacemaker according to claim 5, wherein the biological electrode further comprising a pedestal that is formed between the distal end and a base end of the thin metallic wire and supports the conductive fabric and the thin metallic wire.

11. The cardiac pacemaker according to claim 8, wherein the biological electrode further comprising a pedestal that is formed between the distal end and a base end of the thin metallic wire and supports the conductive fabric and the thin metallic wire.

12. The cardiac pacemaker according to claim 9, wherein the biological electrode further comprising a pedestal that is formed between the distal end and a base end of the thin metallic wire and supports the conductive fabric and the thin metallic wire.

13. A biological electrode comprising:
a conductive fabric formed of base fibers which are filled with a conductor or to which the conductor is adhered;
a thin metallic wire formed into shape of a helix around an axis and covered with the conductive fabric from a side of a distal end in an axis direction; and
a filling material with which a gap between the conductive fabric and the thin metallic wire is filled and configured to support the conductive fabric and the thin metallic wire, wherein the shape of the helix of the thin metallic wire has a convex shape protruding outwardly in the axis direction and the conductive fabric covering the distal end of the thin metallic wire has a convex shape protruding outwardly in the axis direction the conductive fabric is arranged to have a curved surface protruding outwardly, and the conductor is electrically connected with the thin metallic wire.

* * * * *